United States Patent [19]

Philippe et al.

[11] Patent Number: 5,001,156
[45] Date of Patent: Mar. 19, 1991

[54] LIPOPHILIC QUATERNARY AMMONIUM SALICYLATES, THEIR USE IN COSMETICS AND IN DERMOPHARMACY

[75] Inventors: Michel Philippe, Antony; Henri Sebag; Michel Hocquaux, both of Paris; Bernard Jacquet; Jean P. Laugier, both of Antony, all of France

[73] Assignee: L'oreal, Paris, France

[21] Appl. No.: 127,494

[22] Filed: Dec. 1, 1987

[30] Foreign Application Priority Data

Dec. 1, 1986 [FR] France .................. 86 16763

[51] Int. Cl.$^5$ .............. A61K 9/10; A61K 31/14; A61K 31/16; A61K 31/17; A61K 31/185; A61K 31/235; A61K 31/24; C07C 91/26; C07C 101/72; C07C 69/76; C07C 149/40; C07C 125/06; C07C 69/76; C07D 213/46; C07D 265/30; C07D 295/18

[52] U.S. Cl. .................. 514/555; 514/231.2; 514/237.8; 514/238.8; 514/239.2; 514/239.5; 514/299; 514/315; 514/357; 514/358; 514/396; 514/399; 514/532; 514/533; 514/534; 514/538; 514/540; 514/541; 514/542; 514/545; 514/859; 514/880; 514/886; 514/887; 514/912; 514/914; 514/937; 514/852; 544/106; 544/158; 544/159; 544/160; 544/162; 544/168; 544/170; 544/171; 544/175; 544/177; 546/112; 546/184; 546/246; 546/247; 546/248; 546/329; 546/331; 546/334; 546/335; 546/336; 546/337; 546/339; 546/340; 546/341; 546/342; 546/344; 546/346; 546/347; 548/335; 548/341; 560/8; 560/9; 560/11; 560/12; 560/13; 560/15; 560/16; 560/19; 560/24; 560/25; 560/27; 560/29; 560/30; 560/31; 560/33; 560/34; 560/37; 560/38; 560/39; 560/41; 560/42; 560/45; 560/47; 560/49; 560/50; 560/51; 560/53; 560/55; 560/60; 562/429; 562/430; 562/432; 562/439; 562/433; 562/442; 562/451; 562/452; 562/455; 562/459; 562/463

[58] Field of Search .................. 260/501.17; 560/8, 9, 560/11, 12, 13, 15, 16, 19, 34, 37, 38, 39, 41, 42, 45, 47, 49, 50, 51, 53, 55, 60, 24, 25, 27, 29, 30, 31, 33; 514/532, 533, 534, 538, 540, 541, 542, 545, 555, 880, 886, 887, 852, 859, 912, 914, 937; 562/429, 430, 432, 439, 433, 442, 451, 452, 455, 459, 463

[56] References Cited

U.S. PATENT DOCUMENTS

| | | | |
|---|---|---|---|
| 3,879,464 | 4/1975 | Kalopissis et al. | 514/555 |
| 4,009,255 | 2/1977 | Kalopissis et al. | 514/555 |
| 4,096,332 | 6/1978 | Kalopissis et al. | 514/555 |
| 4,220,602 | 9/1980 | Kalopissis et al. | 514/555 |
| 4,436,909 | 3/1984 | Kalopissis et al. | 514/555 |
| 4,695,653 | 9/1987 | Kalopissis et al. | 514/555 |

FOREIGN PATENT DOCUMENTS 0124905 11/1984 European Pat. Off. ............ 514/555

Primary Examiner—Mary C. Lee
Assistant Examiner—J. Richter
Attorney, Agent, or Firm—Fleit, Jacobson, Cohn, Price, Holman & Stern

[57] ABSTRACT

Lipophilic quaternary ammonium salicylate, characterized in that it corresponds to the formula:

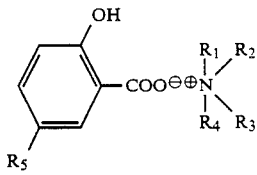

in which:
(i) $R_1$, $R_2$, $R_3$ and $R_4$, which may be identical or different, denote an alkyl or alkylcycloalkyl radical, optionally substituted or interrupted;
(ii) $R_3$ and/or $R_4$ denote(s) a group:
$R_8[OC_2H_3R_7]_n [OCH_2CHOH-CH_2]_p$ in which $0 \leq n \leq 4$ and p denotes 0 or 1; $R_8$ denotes H or an alkyl, alkenyl, alkylcycloalkyl or alkylaryl radical;
(iii) $R_4$ denotes an alkylphenyl radical;
(iv), (v) $R_1$ and $R_2$ can form a saturated or unsaturated aromatic or non-aromatic heterocycle;
(vi) $R_1$, $R_2$ and $R_3$ form polycyclic derivatives with the nitrogen atoms; $R_5$ denotes a group corresponding to the formula:

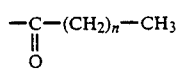

in which n is an integer varying between 0 and 10.

11 Claims, No Drawings

LIPOPHILIC QUATERNARY AMMONIUM SALICYLATES, THEIR USE IN COSMETICS AND IN DERMOPHARMACY

The present invention relates to new lipophilic salicylates containing at least one quaternary ammonium group, the process for preparing them and the pharmaceutical and cosmetic compositions containing them.

The use of various hexadecyltrimethylammonium salts, including the salicylate, as a germicidal agent has been described in the prior art. See in particular SHELTON et al., J.A.C.S. (1946), 68, 753 as well as GAUTIER et al., Bull. Soc. Chim. France (1955), 634 and Broh-Kahn, Intern. Rec. Med. (1960), 173, 219.

The Applicant has just discovered, and this forms the subject of the invention, new lipophilic quaternary ammonium salicylates.

It has found, in particular, that these compounds were especially active as bactericidal and keratolytic agents in the treatment of infectious or non-infectious dermatoses which are possibly of bacterial or fungal origin and/or linked to the implantation of certain yeasts having a pathogenic nature. In particular, these new compounds have the advantage of being able to be used in the treatment of acne, comedones and psoriasis, and of preventing skin infections whose onset is a phenomenon secondary to a cutaneous stress of some kind, such as cuts, burns, solar erythema or various kinds of inflammation. In addition, they have good antidandruff and deodorant properties.

The Applicant has also discovered that certain compounds possess good properties of absorption of light and UV radiation.

In addition, these compounds can be used advantageously in ophthalmology and for the treatment of buccal infections and inflammations of the nasal mucosae, and more generally for the treatment of viral conditions. These compounds possess, moreover, spermicidal properties.

These compounds possess, moreover, good preservative properties. Some of these compounds can be used on account of their surfactant and foam-stabilizing properties.

The Applicant has discovered, in particular, that these new compounds possessed special value in the treatment of acne.

As is well known, acne is a polymorphic skin disorder occurring at puberty and regressing spontaneously in the large majority of cases at about 20 to 25 years of age. In the individuals concerned, acne affects all the areas rich in sebaceous glands (the forehead, the face, wings of the nose, trunk, back) with the exception of the scalp.

Although poorly defined, the etiopathogenesis of acne owes its origin to the formation of a characteristic lesion, the comedo. The latter results from the obstruction of the pilosebaceous duct as a consequence of a dyskeratinization of the region of the infundibilum of the duct.

The major effect of this obstruction is to modify the rheological properties of the sebum and the physicochemical characteristics of the medium, such as pH, oxygen tension, and the like.

This modification permits the hyperproliferation of the resident cutaneous strains, chiefly Propionibacterium acnes, which is an anaerobic or air-tolerant strain.

The consequence of the bacterial hyperproliferation is to release into the medium certain proteases or hyaluronidases of bacterial origin, which cause a lysis of the follicular sac and hence the release of inflammatory compounds within the dermis, and initiate the body's inflammatory type reaction.

While the nature of the inflammatory compounds has not at present been determined, their bacterial origin seems to be in little doubt, accounting for the good therapeutic success of antibacterial compounds, both orally and topically, in inflammatory acne.

For this purpose, antibacterial agents such as antibiotics, for example erythromycin, tetracycline and clindamycin have been recommended very frequently in the treatment of acne. These compounds give excellent results, but their over-zealous use renders the Propionibacterium acnes strains resistant to these same antibiotics, so that repeated treatment may prove to have little effect.

The Applicant has discovered that the new lipophilic quaternary ammonium salicylates had an anti-bacterial activity in vitro, with respect to Propionibacterium acnes, similar to that of the antibiotics used previously, without, however, inducing phenomena of bacterial resistance.

The new lipophilic quaternary ammonium salicylates are especially more active towards Propionibacterium acnes strains than hexadecyltrimethylammonium salicylate, as well as other quaternary ammonium derivatives having an organic counter-anion that are known in the prior art.

The lipophilic quaternary ammonium salicylates according to the invention also have the advantage of not being very irritant to the skin. These new compounds are, moreover, more capable of penetrating the stratum corneum in the case of a topical application.

The subject of the invention is hence, by way of new compounds, lipophilic quaternary salicylates defined below.

Another subject of the invention consists of therapeutic treatment compositions containing the compounds defined above.

The subject of the invention is also a composition and a process for cosmetic treatment based on these compounds.

Other subjects of the invention will emerge on reading the description and examples which follow.

The lipophilic quaternary ammonium salicylates which constitute the main subject of the invention are compounds essentially corresponding to the formula:

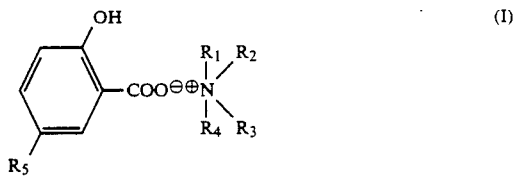

in which:
(i) $R_1$, $R_2$, $R_3$ and $R_4$, which may be identical or different, denote a $C_1$ to $C_{22}$ saturated or unsaturated alkyl or alkylcycloalkyl radical which can optionally be interrupted by one or more groups chosen from ether, thioether, sulphoxide, ester, amide, sulphonamide, carbamate or ureido groups and/or which can bear, at the end of the chain or in the chain, one or more hydroxyl or halogen group(s);
(ii) $R_3$ and/or $R_4$ denote(s) a group:
$R_8[OC_2H_3R_7]_n[OCH_2CHOH-CH_2]_p$ in which: $0 \leq n \leq 4$ and p denotes 0 or 1.

$R_8$ denotes H or a $C_1$ to $C_{18}$ alkyl, alkenyl, alkylcycloalkyl or alkylaryl radical, it being possible for the alkyl groups to be linear or branched and for the aliphatic or aromatic rings optionally to bear one or more $C_1$ to $C_4$ alkyl or alkoxy substituent(s);

$R_7$ denotes H, $CH_3$ or $CH_2OH$.

When $R_7$ denotes $CH_2OH$, $R_8$ is then other than H and p equals 1.

In the other cases, p=0.

The group $(OC_2H_3R_7)$ can denote either or both of the following arrangements:

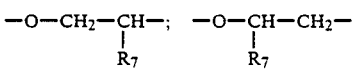

$R_1$ and $R_2$ have the meanings assigned in paragraph (i);

(iii) $R_4$ denotes the group;

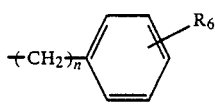

in which n denotes 0 or 1, in which case $R_1$, $R_2$ and $R_3$ have the meanings stated above, $R_6$ denotes a hydrogen, a hydroxyl, a halogen, an alkyl or hydroxyalkyl residue or a $C_1$ to $C_{18}$ acyl residue;

(iv) $R_1$ and $R_2$ form an aromatic heterocycle (in which case $R_3$ is non-existent) corresponding to the formula:

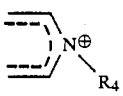

in which $R_4$ has the meanings stated above;

(v) $R_1$ and $R_2$ form a saturated or unsaturated non-aromatic heterocycle, optionally interrupted by an oxygen atom or a nitrogen atom or a sulphur atom; in which case $R_4$ denotes a group defined above and $R_3$ denotes a group also defined in (i);

(vi) $R_1$, $R_2$ and $R_3$ form, together with one or more nitrogen atoms, polycyclic derivatives such as diazabicyclooctane or hexamethylenetetramine, $R_4$ in this case denoting a group defined above under (i) and (iii).

Generally speaking, the ammonium groups are such that at most two of the radicals $R_1$ to $R_4$ consist of 12 or more than 12 consecutive carbon atoms.

In the different cases mentioned above, $R_5$ denotes a group:

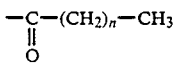

n varying from 0 to 10 inclusive.

The compounds according to the invention are preferably prepared from a salt such as, more especially, the corresponding quaternary ammonium carbonate, solubilized in alcoholic medium and preferably in methanol, to which is added the chosen lipophilic salicyclic acid derivative, also solubilized in an alcohol such as ethanol or methanol or alternatively in an ether such as tetrahydrofuran. The reaction starts by itself and is followed by the evolution of carbon dioxide.

Preferred compounds are chosen, in particular, from the following compounds: hexadecyltrimethylammonium 5-octanoylsalicylate, hexadecyltrimethylammonium 5-decanoylsalicylate, hexadecyltrimethylammonium 5-dodecanoylsalicylate, hexadecylpyridinium 5-octanoylsalicylate, hexadecylpyridinium 5-decanoylsalicylate, hexadecylpyridinium 5-dodecanoylsalicylate, benzyldimethylhexadecylammonium 5-octanoylsalicylate, benzyldimethylhexadecylammonium 5-decanoylsalicylate, benzyldimethylhexadecylammonium 5-dodecanoylsalicylate, benzyltrimethylammonium 5-decanoylsalicylate, hexadecyldimethyl(hydroxyethyl)ammonium 5-decanoylsalicylate, tetramethylammonium 5-dodecanoylsalicylate, dodecylethyldimethylammonium 5-decanoylsalicylate, trimethyl-($\beta$-hydroxyethyl)-ammonium 5-decanoylsalicylate, trimethyl-($\beta$-hydroxyethyl)-ammonium 5-dodecanoylsalicylate, N-hexadecyl-N-methylimidazolinium 5-dodecanoylsalicylate, N-dodecyl-N-methylmorpholinium 5-decanoylsalicylate, N-methyl-N-octylpiperidinium 5-dodecanoylsalicylate, 1'-azonia-4'-azabicyclo[2.2.2]octylhexadecane 5-dodecanoylsalicylate, benzethonium 5-octanoylsalicylate, benzethonium 5-dodecanoylsalicylate, N-(3-chloroallyl)hexaminium 5-octanoylsalicylate and N-(3-chloroallyl)hexaminium 5-dodecanoylsalicylate.

The pharmaceutical compositions which are the subject of the invention are essentially characterized in that they are topical compositions containing at least one of the compounds corresponding to the formula (I) above in a pharmaceutically acceptable medium that is suitable for topical application.

These compositions are especially suitable for the treatment of various dermatoses such as acne.

The compositions can take the form of an aqueous or anhydrous solution or dispersion, or alternatively the form of an emulsion or suspension, containing at least one compound corresponding to the formula (I) in concentrations between 0.001 and 15% by weight based on the total weight of the composition, and preferably between 0.05 and 5%.

These compositions can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives, in the proportion of 0.5 to 20% by weight based on the total weight of the composition. They can also contain gums such as xanthan, guar or carob gum or gum arabic, or alternatively polyethylene glycols, bentones and montmorillonites, and the like.

These compositions according to the invention can also contain, in combination, antiacne agents such as retinoic derivatives, antibacterial agents, anti-inflammatories, and steroids having a non-hormonal action, in particular pregnenolone, which is already known for the treatment and care of the skin, whose properties are described in U.S. Pat. No. 2,791,534.

It is possible to add, if necessary, an adjuvant chosen from antioxidants, surfactants, other preservatives, film-forming, keratolytic or comedolytic agents, perfumes and colourings.

For example, among antioxidants, t-butylhydroquinone, butylated hydroxyanisole, butylated hydroxytoluene and α-tocopherol and its derivatives may be mentioned.

The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

A subject of the invention resides in the use of the compounds of the formula I for the preparation of such compositions intended for the treatment of dermatoses.

The compositions according to the invention can also be used for the cosmetic treatment of the skin, in particular as comedolytic, keratolytic, antisun or verrulytic agents, or as agents for treating the hair or scalp.

These compositions can assume forms similar to those mentioned above, and can contain adjuvants customarily used in cosmetics in compositions intended for the care and cosmetic treatment of the skin.

The process for cosmetic treatment consists in applying such a composition on the skin.

The antibacterial activity of the compounds according to the invention was studied by the dilution method in order to determine the Minimal Inhibitory Concentration (MIC) according to the method described and employed by G. A. DENYS et al., Antimicrobial Agents and Chemotherapy (1983) 23, 335–337, and J. J. LEYDEN et al., J. Am. Acad. Dermatol. (1983) 8 (1) 41-5, using Propionibacterium acnes strain ATCC 6919 as the strain.

The minimal inhibitory concentrations (MIC), expressed in μg/ml (DMSO), of the lipophilic quaternary ammonium salicylates according to the invention are shown in Table 1.

TABLE I

MIC Tests

| No | Name of the compound | on ATCC 6919 MIC (μg/ml) | $R_1$ | $R_2$ | $R_3$ | $R_4$ | $R_5$ |
|---|---|---|---|---|---|---|---|
| 1 | N-Hexadecyl-N,N,N-trimethylammonium salicylate* | 21 | —CH$_3$ | —CH$_3$ | —CH$_3$ | n-C$_{16}$H$_{33}$ | H |
| 2 | Hexadecyltrimethylammonium laurate* | 26 | | | | | ** |
| 3 | Hexadecyltrimethylammonium stearate* | 25 | | | | | ** |
| 4 | Hexadecyltrimethylammonium 5-octanoylsalicylate | 8 | —CH$_3$ | —CH$_3$ | —CH$_3$ | n-C$_{16}$H$_{33}$ | —CO-nC$_7$H$_{15}$ |
| 5 | Hexadecyltrimethylammonium 5-decanoylsalicylate | 2.3 | —CH$_3$ | —CH$_3$ | —CH$_3$ | n-C$_{16}$H$_{33}$ | —CO-nC$_9$H$_{19}$ |
| 6 | Hexadecyltrimethylammonium 5-dodecanoylsalicylate | 3.2 | —CH$_3$ | —CH$_3$ | —CH$_3$ | n-C$_{16}$H$_{33}$ | —CO-nC$_{11}$H$_{23}$ |
| 7 | Hexadecylpyridinium 5-octanoylsalicylate | 2.4 | pyridinium | | | n-C$_{16}$H$_{33}$ | —CO-nC$_7$H$_{15}$ |
| 8 | Hexadecylpyridinium 5-decanoylsalicylate | 1.2 | pyridinium | | | n-C$_{16}$H$_{33}$ | —CO-nC$_9$H$_{19}$ |
| 9 | Hexadecylpyridinium 5-dodecanoylsalicylate | 1.2 | pyridinium | | | n-C$_{16}$H$_{33}$ | —CO-nC$_{11}$H$_{23}$ |
| 10 | Benzyldimethylhexadecylammonium 5-octanoylsalicylate | 0.54 | —CH$_3$ | —CH$_3$ | n-C$_{16}$H$_{33}$ | —CH$_2$-C$_6$H$_5$ | —CO-nC$_7$H$_{15}$ |
| 11 | Benzyldimethylhexadecylammonium 5-decanoylsalicylate | 1.5 | —CH$_3$ | —CH$_3$ | n-C$_{16}$H$_{33}$ | —CH$_2$-C$_6$H$_5$ | —CO-nC$_9$H$_{19}$ |
| 12 | Benzyldimethylhexadecylammonium 5-dodecanoylsalicylate | 1 | —CH$_3$ | —CH$_3$ | n-C$_{16}$H$_{33}$ | —CH$_2$-C$_6$H$_5$ | —CO-nC$_{11}$H$_{23}$ |

TABLE I-continued

MIC Tests

| No | Name of the compound | on ATCC 6919 MIC (μg/ml) | $R_1$ | $R_2$ | $R_3$ | $R_4$ | $R_5$ |
|---|---|---|---|---|---|---|---|
| 13 | Benzyltrimethylammonium 5-decanoylsalicylate | 3.2 | $-CH_3$ | $-CH_3$ | $-CH_3$ | $-CH_2-C_6H_5$ | $-CO-nC_9H_{19}$ |
| 14 | Hexadecyldimethyl-(hydroxyethyl)ammonium 5-decanoylsalicylate | 3.6 | $-CH_3$ | $-CH_3$ | $-CH_2CH_2OH$ | $n-C_{16}H_{33}$ | $-CO-nC_9H_{19}$ |
| 15 | Tetramethylammonium 5-dodecanoylsalicylate | 2.5 | $-CH_3$ | $-CH_3$ | $-CH_3$ | $-CH_3$ | $-CO-nC_{11}H_{23}$ |
| 16 | Dodecylethyldimethylammonium 5-decanoylsalicylate | 6.2 | $-CH_3$ | $-CH_3$ | $-C_2H_5$ | $n-C_{12}H_{25}$ | $-CO-nC_9H_{19}$ |
| 17 | Trimethyl-(β-hydroxyethyl)ammonium 5-decanoylsalicylate | 11 | $-CH_3$ | $-CH_3$ | $-CH_3$ | $-C_2H_4OH$ | $-CO-nC_9H_{19}$ |
| 18 | Trimethyl-(β-hydroxyethyl)ammonium 5-dodecanoylsalicylate | 4.8 | $-CH_3$ | $-CH_3$ | $-CH_3$ | $-C_2H_4OH$ | $-CO-nC_{11}H_{23}$ |
| 19 | N-(2-Hydroxyethyl)-N,N,N-trimethylammonium salicylate* | >100 | $-CH_3$ | $-CH_3$ | $-CH_3$ | $-CH_2CH_2OH$ | H |
| 20 | N-Hexadecyl-N-methylimidazolinium 5-dodecanoylsalicylate | 13.5 | (imidazolinium ring) | | | $n-C_{16}H_{33}$ | $-CO-nC_{11}H_{23}$ |
| 21 | N-Dodecyl-N-methylmorpholinium 5-decanoylsalicylate | 9 | (morpholinium ring) | | $-CH_3$ | $n-C_{12}H_{25}$ | $-CO-nC_9H_{19}$ |
| 22 | N-Methyl-N-octylpiperidinium 5-dodecanoylsalicylate | 4.9 | (piperidinium ring) | | $-CH_3$ | $n-C_8H_{17}$ | $-CO-nC_{11}H_{23}$ |
| 23 | 1'-Azonia-4'-azabicyclo[2.2.2]octylhexadecane 5-dodecanoylsalicylate | 1.5 | (DABCO ring) | | | $n-C_{16}H_{33}$ | $-CO-nC_{11}H_{23}$ |
| 24 | Benzethonium 5-octanoylsalicylate | 1.2 | $-CH_3$ | $-CH_3$ | $C_8H_{17}$-φ-$(OCH_2CH_2)_2-$ | $-CH_2-C_6H_5$ | $-CO-nC_7H_{15}$ |
| 25 | Benzethonium 5-dodecanoylsalicylate | 2 | $-CH_3$ | $-CH_3$ | $C_8H_{17}$-φ-$(OCH_2CH_2)_2-$ | $-CH_2-C_6H_5$ | $-CO-nC_{11}H_{23}$ |

*Controls
**Not corresponding to the formula I

It emerges from this table that the lipophilic salicylates according to the invention are markedly more active with respect to the Propionibacterium acnes strain than the salicylates previously recommended in the prior art.

The examples which follow are designed to illustrate on the one hand the processes for the preparation of the compounds according to the invention, and on the other hand pharmaceutical and cosmetic compositions employing these compounds.

PREPARATION EXAMPLE 1

Preparation of N-hexadecyl-N,N,N-trimethylammonium 5-octanoylsalicylate: compound no. 4 (Table I).

2 g (7.57 mmol) of 5-octanoylsalicylic acid, dissolved beforehand in 15 ml of methanol, are added to a solution of 2.62 g (4.16 mmol) of hexadecyltrimethylammonium carbonate dissolved in 15 ml of methanol; the mixture is stirred for 1 hour at room temperature and the solvent is then evaporated off, and the white solid residue obtained is recrystallized in an acetone/diethyl ether mixture to give 3.8 g (91.5% yield) of hexadecyltrimethylammonium 5-octanoylsalicylate.

M.p. 130° C. (acetone/diethyl ether) Elementary analysis: $C_{34}H_{61}NO_4$; M=547.9

|  | C | H | N |
|---|---|---|---|
| Calculated % | 74.54 | 11.22 | 2.56 |
| Found % | 74.48 | 11.31 | 2.62 |

The $^1H$ and $^{13}C$ NMR spectra confirm the expected structure with the characteristic values for the ammonium cation and the 5-octanoylsalicylate anion.

PREPARATION EXAMPLE 2

Preparation of N-hexadecyl-N,N,N-trimethylammonium 5-decanoylsalicylate: compound no. 5.

2 g (6.85 mmol) of 5-decanoylsalicylic acid, dissolved beforehand in 15 ml of ethanol, are added to a solution of 2.2 g (3.5 mmol) of hexadecyltrimethylammonium carbonate dissolved in 15 ml of methanol; the mixture is stirred for 1 hour at room temperature, the solvents are then evaporated off and the white solid residue obtained is recrystallized in an acetone/diethyl ether mixture to give 3.8 g (96% yield) of hexadecyltrimethylammonium 5-decanoylsalicylate.

M.p. 130° C. (acetone/diethyl ether) Elementary analysis: $C_{36}H_{65}NO_4$; M=575.9

|  | C | H | N |
|---|---|---|---|
| Calculated % | 75.08 | 11.37 | 2.43 |
| Found % | 75.05 | 11.42 | 2.44 |

The $^1H$ and $^{13}C$ NMR spectra confirm the expected structure with the characteristic values for the quaternary ammonium cation and the 5-decanoylsalicylate anion.

PREPARATION EXAMPLE 3

Preparation of N-hexadecyl-N,N,N-trimethylammonium 5-dodecanoylsalicylate: compound no. 6.

2 g (6.25 mmol) of 5-dodecanoylsalicylic acid, dissolved beforehand in 15 ml of ethanol, are added to a solution of 2 g (3.18 mmol) of hexadecyltrimethylammonium carbonate dissolved in 15 ml of methanol; the mixture is stirred for 1 hour at room temperature, the solvents are then evaporated off and the white solid residue obtained is recrystallized in an acetone/diethyl ether mixture to give 3.5 g (93% yield) of hexadecyltrimethylammonium 5-dodecanoylsalicylate.

M.p. 130° C. (acetone/diethyl ether) Elementary analysis: $C_{38}H_{69}NO_4$; M=604

|  | C | H | N |
|---|---|---|---|
| Calculated % | 75.57 | 11.52 | 2.32 |
| Found % | 75.17 | 11.61 | 2.5 |

The $^{13}C$ NMR spectrum confirms the expected structure with the characteristic values for the quaternary ammonium cation and the 5-dodecanoylsalicylate anion.

The UV spectrum (ethanol) shows an absorption $\lambda_{max}=280$ nm; the molar extinction coefficient $\epsilon=14080$.

PREPARATION EXAMPLE 4

Preparation of N-hexadecylpyridinium 5-octanoylsalicylate monohydrate: compound no. 7.

2 g (7.57 mmol) of 5-octanoylsalicylic acid, dissolved beforehand in 15 ml of methanol, are added to a solution of 2.5 g (3.79 mmol) of hexadecylpyridinium carbonate dissolved in 15 ml of methanol; the mixture is stirred for 1 hour at room temperature, the brown crude residue obtained is then filtered off and the filtrate is evaporated to dryness to give 4.2 g (98% yield) of hexadecylpyridinium 5-octanoylsalicylate.

Elementary analysis: $C_{36}H_{57}NO_4.1H_2O$; M=585.9

|  | C | H | N |
|---|---|---|---|
| Calculated % | 73.8 | 10.15 | 2.39 |
| Found % | 73.22 | 9.77 | 2.31 |

The $^{13}C$ NMR spectrum confirms the expected structure with the characteristic values for the quaternary ammonium cation and the 5-octanoylsalicylate anion.

The UV spectrum (ethanol) shows an absorption $\lambda_{max}=279$ nm; the molar extinction coefficient $\epsilon=21450$.

PREPARATION EXAMPLE 5

Preparation of N-hexadecylpyridinium 5-decanoylsalicylate sesquihydrate; compound no. 8.

2 g (6.85 mmol) of 5-decanoylsalicylic acid, dissolved beforehand in 15 ml of ethanol, are added to a solution of 2.3 g (3.44 mmol) of hexadecylpyridinium carbonate dissolved in 15 ml of methanol; the mixture is stirred for 1 hour at room temperature, the solvents are then evaporated off and the brown residue obtained is recrystallized in an acetone/diethyl ether mixture to give 3.9 g (96% yield) of hexadecylpyridinium 5-decanoylsalicylate.

M.p. 73° C. (acetone/diethyl ether) Elementary analysis: $C_{38}H_{61}NO_4.1.5H_2O$; M=622.9

|  | C | H | N |
|---|---|---|---|
| Calculated % | 73.27 | 10.36 | 2.25 |
| Found % | 73.64 | 9.64 | 1.82 |

The $^{13}C$ NMR spectrum confirms the expected structure with the characteristic values for the aromatic quaternary ammonium cation and 5-decanoylsalicylate.

PREPARATION EXAMPLE 6

Preparation of N-hexadecylpyridinium 5-dodecanoylsalicylate hydrate: compound no. 9.

2 g (6.25 mmol) of 5-dodecanoylsalicylic acid, dissolved beforehand in 15 ml of ethanol, are added to a solution of 2.1 g (3.14 mmol) of hexadecylpyridinium carbonate dissolved in 15 ml of methanol; the mixture is stirred for 1 hour at room temperature, the solvents are then evaporated off and the brown residue obtained is recrystallized in an acetone/diethyl ether mixture to give 3.7 g (95% yield) of hexadecylpyridinium 5-dodecanoylsalicylate.

M.p. 79° C. (acetone/diethyl ether) Elementary analysis: $C_{40}H_{65}NO_4.1H_2O$; M=642

|  | C | H | N |
|---|---|---|---|
| Calculated % | 74.84 | 10.52 | 2.18 |
| Found % | 74.61 | 10.12 | 1.96 |

The $^{13}C$ NMR spectrum confirms the expected structure with the characteristic values for the aromatic quaternary ammonium cation and 5-dodecanoylsalicylate.

The UV spectrum (ethanol) shows an absorption $\lambda_{max}=279$ nm; the molar extinction coefficient $\epsilon=18910$.

PREPARATION EXAMPLE 7

Preparation of N-benzyl-N,N-dimethyl-N-hexadecylammonium 5-octanoylsalicylate: compound no. 10.

2 g (7.57 mmol) of 5-octanoylsalicylic acid, dissolved beforehand in 15 ml of methanol, are added to a solution of 3 g (3.84 mmol) of benzyldimethylhexadecylammonium carbonate dissolved in 15 ml of methanol; the mixture is stirred for 1 hour at room temperature, the solvent is then evaporated off and the white residue is recrystallized in an acetone/diethyl ether mixture to give 4.5 g (95% yield) of benzyldimethylhexadecylammonium 5-octanoylsalicylate.

M.p. 114° C. (acetone/diethyl ether) Elementary analysis: $C_{40}H_{65}NO_4$; M=623.9

|  | C | H | N |
|---|---|---|---|
| Calculated % | 77.00 | 10.50 | 2.24 |
| Found % | 77.02 | 10.58 | 2.38 |

The $^{13}C$ NMR spectrum confirms the expected structure with the characteristic signals of the quaternary ammonium cation and 5-octanoylsalicylate.

The compounds of Examples nos. 8 to 21 are prepared in a manner similar to that described in Examples 1 to 7.

PREPARATION EXAMPLE 8

Preparation of N-benzyl-N,N-dimethyl-N-hexadecylammonium 5-decanoylsalicylate: compound no. 11.

M.p. 113° C. (acetone/diethyl ether) Elementary analysis: $C_{42}H_{69}NO_4$; M=652

|  | C | H | N |
|---|---|---|---|
| Calculated % | 77.37 | 10.67 | 2.15 |
| Found % | 77.22 | 10.69 | 2.25 |

PREPARATION EXAMPLE 9

Preparation of N-benzyl-N,N-dimethyl-N-hexadecylammonium 5-dodecanoylsalicylate: compound no. 12.

M.p. 117° C. (acetone/diethyl ether) Elementary analysis: $C_{44}H_{73}NO_4$; M=680.08

|  | C | H | N |
|---|---|---|---|
| Calculated % | 77.71 | 10.82 | 2.06 |
| Found % | 77.15 | 10.81 | 2.08 |

The UV spectrum (ethanol) shows an absorption $\lambda_{max}=281$ nm; the molar extinction coefficient $\epsilon=17720$.

PREPARATION EXAMPLE 10

Preparation of N-benzyl-N,N,N-trimethylammonium 5-decanoylsalicylate: compound no. 13.

M.p. 135° C. (acetone/diethyl ether) Elementary analysis: $C_{27}H_{39}NO_4$; M=441.6

|  | C | H | N |
|---|---|---|---|
| Calculated % | 73.43 | 8.9 | 3.17 |
| Found % | 73.01 | 8.74 | 3.18 |

PREPARATION EXAMPLE 11

Preparation of N-hexadecyl-N,N-dimethyl-N-($\beta$-hydroxyethyl)ammonium 5-decanoylsalicylate: compound no. 14.

Elementary analysis: $C_{37}H_{68}NO_5 \cdot \frac{1}{2}H_2O$; M=615.96

|  | C | H | N |
|---|---|---|---|
| Calculated % | 72.15 | 11.29 | 2.12 |
| Found % | 72.51 | 10.85 | 2.27 |

PREPARATION EXAMPLE 12

Preparation of N,N,N,N-tetramethylammonium 5-dodecanoylsalicylate: compound no. 15.

M.p. 97° C. (acetone/diethyl ether) Elementary analysis: $C_{23}H_{40}NO_4$: M=390.15

|  | C | H | N |
|---|---|---|---|
| Calculated % | 70.8 | 10.33 | 3.59 |
| Found % | 70.27 | 9.87 | 3.38 |

PREPARATION EXAMPLE 13

Preparation of trimethyl-($\beta$-hydroxyethyl)ammonium 5-dodecanoylsalicylate: compound no. 18.

M.p. 67° C. (methanol/diethyl ether) Elementary analysis: $C_{24}H_{41}NO_5$; M=423.6

|  | C | H | N |
|---|---|---|---|
| Calculated % | 68.05 | 9.76 | 3.31 |
| Found % | 68.09 | 9.59 | 2.69 |

UV spectrum (ethanol): $\lambda_{max}=280$ nm; $\epsilon=16640$.

PREPARATION EXAMPLE 14

Preparation of trimethyl-($\beta$-hydroxyethyl)ammonium 5-decanoylsalicylate: compound no. 17.

Elementary analysis: $C_{22}H_{35}NO_5 \cdot 3/4H_2O$: M=407.6

|  | C | H | N |
|---|---|---|---|
| Calculated % | 64.82 | 9.51 | 3.43 |
| Found % | 64.75 | 9.36 | 3.01 |

PREPARATION EXAMPLE 15

Preparation of dimethylethyldodecylammonium 5-decanoylsalicylate: compound no. 16.

M.p. 65° C. (acetone/diethyl ether) Elementary analysis: $C_{33}H_{59}NO_4.H_2O$; M=551.9

|  | C | H | N |
|---|---|---|---|
| Calculated % | 71.8 | 11.14 | 2.62 |
| Found % | 72.07 | 10.74 | 2.33 |

PREPARATION EXAMPLE 16

Preparation of N-hexadecyl-N-methylimidazolinium 5-dodecanoylsalicylate: compound no. 20.

M.p. 82° C. (acetone/diethyl ether) Elementary analysis: $C_{39}H_{66}N_2O_4.1.5H_2O$; M=654

|  | C | H | N |
|---|---|---|---|
| Calculated % | 71.62 | 10.62 | 4.28 |
| Found % | 71.82 | 10.68 | 4.02 |

UV spectrum (ethanol): $\lambda_{max}$=281 nm; $\epsilon$=15385

PREPARATION EXAMPLE 17

Preparation of 1'-azonia-4'-azabicyclo[2.2.2]octylhexadecane 5-dodecanoylsalicylate: compound no. 23.

M.p. 96° C. (acetone/diethyl ether) Elementary analysis: $C_{41}H_{72}N_2O_4.H_2O$; M=675

|  | C | H | N |
|---|---|---|---|
| Calculated % | 72.95 | 11.04 | 4.15 |
| Found % | 72.57 | 10.93 | 4.3 |

PREPARATION EXAMPLE 18

Preparation of N-methyl-N-octylpiperidinium 5-dodecanoylsalicylate: compound no. 22.

M.p. 45° C. (acetone/diethyl ether) Elementary analysis: $C_{33}H_{57}NO_4.0.5H_2O$; M=540.9

|  | C | H | N |
|---|---|---|---|
| Calculated % | 73.28 | 10.81 | 2.59 |
| Found % | 73.31 | 11.02 | 2.7 |

PREPARATION EXAMPLE 19

Preparation of N-dodecyl-N-methylmorpholinium 5-decanoylsalicylate: compound no. 21.

M.p. 78° C. (acetone/diethyl ether) Elementary analysis: $C_{34}H_{59}NO_5$; M=561.8

|  | C | H | N |
|---|---|---|---|
| Calculated % | 72.68 | 10.58 | 2.49 |
| Found % | 72.58 | 10.68 | 2.6 |

PREPARATION EXAMPLE 20

Preparation of benzethonium 5-octanoylsalicylate.

2.2 g (8.4 mmol) of 5-octanoylsalicylic acid, dissolved beforehand in 100 ml of methanol, are added to a solution of 3.7 g (4.2 mmol) of benzethonium carbonate dissolved in 100 ml of methanol; the mixture is stirred for 1 hour at room temperature, the solution is then filtered and the filtrate is evaporated to dryness to give 5.5 g (98% yield) of benzethonium 5-octanoylsalicylate.

Elementary analysis: $C_{42}H_{61}NO_6.2H_2O$; MW=712

|  | C | H | N |
|---|---|---|---|
| Calculated % | 70.85 | 9.20 | 1.97 |
| Found % | 70.93 | 9.07 | 2.07 |

The $^{13}$C NMR spectrum confirms the expected structure with the characteristic values for the quaternary ammonium cation and the octanoylsalicylate anion.

PREPARATION EXAMPLE 21

Preparation of benzethonium 5-dodecanoylsalicylate.

2 g (6.4 mmol) of 5-dodecanoylsalicylic acid, dissolved beforehand in 100 ml of ethanol, are added to a solution of 2.82 g (3.2 mmol) of benzethonium carbonate dissolved in 100 ml of methanol; the mixture is stirred for 1 hour at room temperature, the solution is then filtered and the filtrate is evaporated to dryness to give 4.5 g (97% yield) of benzethonium 5-dodecanoylsalicylate.

Elementary analysis: $C_{46}H_{69}NO_6.H_2O$; MW=750

|  | C | H | N |
|---|---|---|---|
| Calculated % | 73.66 | 9.54 | 1.87 |
| Found % | 73.60 | 9.48 | 1.85 |

The $^{13}$C NMR spectrum confirms the expected structure with the characteristic values for the quaternary ammonium cation and the 5-dodecanoylsalicylate anion.

The term benzethonium denotes: N,N-dimethyl-N-[2-{2-[4-(1,1,3,3-tetramethylbutyl)phenoxy]-ethoxy}ethyl]benzenemethaminium, or benzyldimethyl-[2-{2-[p-(1,1,3,3-tetramethylbutyl)phenoxy]-ethoxy}ethyl]ammonium.

The examples which follow are designed to illustrate more especially pharmaceutical or cosmetic compositions employing the compounds according to the invention.

Pharmaceutical and cosmetic compositions

EXAMPLE 1

The following composition is prepared:

| Hydroxypropylcellulose | 1.5 g |
|---|---|
| Hexadecyltrimethylammonium 5-decanoylsalicylate | 3.0 g |
| Isopropanol | qs 100 g |

EXAMPLE 2

The following composition is prepared:

| Hydroxypropylcellulose | 1.5 g |
|---|---|
| Ethyl lactate | 15.0 g |
| Hexadecyltrimethylammonium 5-dodecanoylsalicylate | 2.0 g |
| Isopropanol | qs 100 g |

EXAMPLE 3

The following composition is prepared:

| Hydroxypropylcellulose | 1.0 g |
|---|---|
| Butylated hydroxytoluene | 0.02 g |

| | |
|---|---|
| -continued | |
| Benzyltrimethylammonium 5-decanoyl-salicylate | 0.5 g |
| Ethanol | qs 100 g |

EXAMPLE 4

The following composition is prepared:

| | |
|---|---|
| Hydroxypropylcellulose | 1.5 g |
| Butylated hydroxytoluene | 0.01 g |
| $C_8$–$C_{12}$ fatty acid triglycerides | 10.0 g |
| Hexadecylpyridinium 5-dodecanoylsalicylate | 5.0 g |
| Isopropanol | qs 100 g |

The compositions of Examples 1 to 4 take the form of a gel, and are intended especially for the topical treatment of acne.

EXAMPLE 5

The following composition is prepared:

| | |
|---|---|
| Isopropanol | 46.0 g |
| Hexadecyltrimethylammonium 5-dodecanoyl-salicylate | 5.0 g |
| $C_8$–$C_{12}$ fatty acid triglycerides | 49.0 g |

EXAMPLE 6

The following composition is prepared:

| | |
|---|---|
| Ethanol | 69.0 g |
| Ethyl lactate | 10.0 g |
| Hexadecylpyridinium 5-decanoyl-salicylate | 1.0 g |
| $C_8$–$C_{12}$ fatty acid triglycerides | 20.0 g |

EXAMPLE 7

The following composition is prepared:

| | |
|---|---|
| Isopropanol | 47.0 g |
| Acetone | 10.0 g |
| Ethyl lactate | 10.0 g |
| Benzyltrimethylammonium 5-decanoyl-salicylate | 3.0 g |
| $C_8$–$C_{12}$ fatty acid triglycerides | 30.0 g |

EXAMPLE 8

The following composition is prepared:

| | |
|---|---|
| Ethanol | 95.08 g |
| Butylated hydroxytoluene | 0.02 g |
| Hexadecyltrimethylammonium 5-octanoyl-salicylate | 4.0 g |

These compositions of Examples 5, 6, 7 and 8 take the form of a lotion which is particularly effective in the treatment of acne.

EXAMPLE 9

The following composition is prepared:

| | |
|---|---|
| White vaseline | 50.0 g |
| Liquid paraffin | 15.0 g |
| Refined paraffin wax | 32.0 g |
| Hexadecyltrimethylammonium 5-dodecanoyl-salicylate | 3.0 g |

This composition takes the form of a stick which is suitable for the treatment of acne.

EXAMPLE 10

| | |
|---|---|
| White vaseline | 50.0 g |
| Liquid paraffin | 13.0 g |
| Refined paraffin wax | 32.0 g |
| Trimethyl-($\beta$-hydroxyethyl)ammonium 5-dodecanoylsalicylate | 5.0 g |

This composition takes the form of a stick which is suitable for protecting the lips against solar radiation.

We claim:

1. Lipophilic quaternary ammonium salicylate, corresponding to the formula:

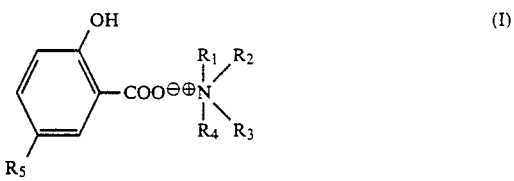

in which (i) $R_1$, $R_2$, $R_3$ and $R_4$, which may be identical or different, denote a $C_1$ to $C_{22}$ alkyl or alkylcycloalkyl radical or a $C_1$ to $C_{22}$ alkyl or alkylcycloalkyl radical interrupted by one or more ether, thioether, sulphoxide, ester, amide, sulphonamide, carbamate or ureido groups or which bears, at the end of the chain or in the chain, one or more hydroxyl or halogen group;

(ii) $R_3$ or $R_4$ denote a group: $R_8\text{---}(OC_2H_3R_7)_{\overline{n}}(OCH_2\text{-}CHOH\text{---}CH_2)_p$ in which $0 > n \leq 4$ and p denotes 0 or 1;

$R_8$ denotes H or a $C_1$ to $C_{18}$ alkyl, alkenyl, alkylcycloalkyl or alkylaryl radical, it being possible for the alkyl groups to be linear or branched and for the aliphatic or aromatic rings to bear one or more $C_1$ to $C_4$ alkyl or alkoxy substituent;

$R_7$ denotes H, $CH_3$ or $CH_2OH$;

when $R_7$ denotes $CH_2OH$, $R_8$ is then other than H and p equals in the other cases, p=0;

the group ($OC_2H_3R_7$) can denote either or both of the following formulas:

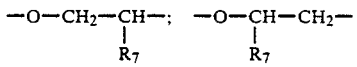

$R_1$ and $R_2$ have the meanings recited in paragraph (i);

or (iii) $R_4$ denotes the group:

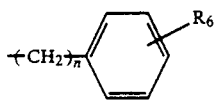

in which n denotes 0 or 1; $R_1$, $R_2$ and $R_3$ having the same meanings as in paragraph (i); $R_6$ denotes a hydrogen, a hydroxyl, a halogen, an alkyl or hydroxyalkyl residue or a $C_1$ to $C_{18}$ acyl residue; and $R_5$ denotes a group corresponding to the formula:

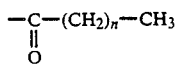

in which n is an integer varying between 0 and 10.

2. Lipophilic quaternary ammonium salicylate according to claim 1, wherein $R_4$ denotes a benzyl group and $R_1$, $R_2$ and $R_3$ have the meanings recited in paragraph (i).

3. Lipophilic quaternary ammonium salicylate of claim 1, selected from the group consisting of: hexadecyltrimethylammonium 5-octanoylsalicylate, hexadecyltrimethylammonium 5-decanoylsalicylate, hexadecyltrimethylammonium 5-dodecanoylsalicylate, benzyldimethylhexadecylammonium 5-octanoylsalicylate, benzyldimethylhexadecylammonium 5-decanoylsalicylate, benzyldimethylhexadecylammonium 5-dodecanoylsalicylate, benzyltrimethylammonium 5-decanoylsalicylate, hexadecyldimethyl(hydroxyethyl)ammonium 5-decanoylsalicylate, tetramethylammonium 5-dodecanoylsalicylate, dodecylethyldimethylammonium 5-decanoylsalicylate, trimethyl-($\beta$-hydroxyethyl)ammonium 5-decanoylsalicylate, trimethyl-($\beta$-hydroxyethyl)ammonium 5-dodecanoylsalicylate,-N-benzethonium 5-octanoylsalicylate, benzethonium 5-dodecanoylsalicylate, 5-octanoylsalicylate and N-(3-chloroallyl)hexaminium 5-dodecanoylsalicy.

4. Topical composition intended for the treatment of dermatoses or skin disorders containing in a pharmaceutically or cosmetically acceptable medium at least one lipophilic quaternary ammonium salicylate of formula (I):

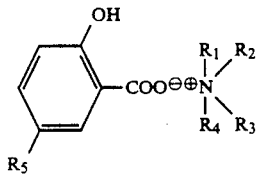

in which
(i) $R_1$, $R_2$, $R_3$ and $R_4$, which may be identical or different, denote a $C_1$ to $C_{22}$ alkyl or alkylcycloalkyl radical or a $C_1$ to $C_{22}$ alkyl or alkylcycloalkyl radical interrupted by one or more ether, thioether, sulphoxide, ester, amide, sulphonamide, carbamate or ureido groups or which bears, at the end of the chain or in the chain, one or more hydroxyl or halogen group;

(ii) $R_3$ or $R_4$ denote a group: 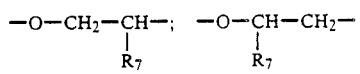
in which
$0 \leq n \leq 4$ and p denotes 0 or 1;

$R_8$ denotes H or a $C_1$ to $C_{18}$ alkyl, alkenyl, alkylcycloalkyl or alkylaryl radical, it being possible for the alkyl groups to be linear or branched and for the aliphatic or aromatic rings to bear one or more $C_1$ to $C_4$ alkyl or alkoxy substituent;

$R_7$ denotes H, $CH_3$ or $CH_2OH$;

when $R_7$ denotes $CH_2OH$, $R_8$ is then other than H and p equals 1;

in the other cases, p=0;

the group ($OC_2H_3R_7$) can denote either or both of the following formulas:

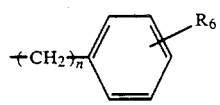

$R_1$ and $R_2$ have the meanings recited in paragraph (i); or (iii) $R_4$ denotes the group:

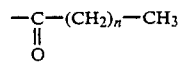

in which n denotes 0 or 1; $R_1$, $R_2$ and $R_3$ having the same meanings as in paragraph (i); $R_6$ denotes a hydrogen, a hydroxyl, a halogen, an alkyl or hydroxyalkyl residue or a $C_1$ to $C_{18}$ acyl residue; and $R_5$ denotes a group corresponding to the formula:

$$-\underset{\underset{O}{\|}}{C}-(CH_2)_n-CH_3$$

in which n is an integer varying between 0 and 10.

5. Composition according to claim 4, containing in combination with the compound of formula (I), at least one other antiacne agent selected from the group consisting of pregnenolone, retinoic derivatives, antibiotics and anti-inflammatories.

6. Composition according to claim 4 in the form of a solution, anhydrous dispersion, emulsion or suspension, containing the lipophilic quaternary ammonium salicylate of formula (I) at a concentration of between 0.001 and 15% by weight based on the total weight of the composition.

7. A method of treating acne comprising applying to the affected area of skin a composition comprising an effective amount of at least one compound of claim 1 and a pharmaceutically acceptable carrier.

8. A method of treating dandruff comprising applying to the scalp a composition comprising at least one compound of claim 1 and a pharmaceutically acceptable carrier.

9. A method of treating warts comprising applying to a wart a composition comprising an effective amount of at least one compound of claim 1 and a pharmaceutically acceptable carrier.

10. A method of treating solar erythema comprising applying to the affected area of skin a composition comprising an effective amount of at least one compound of claim 1 and a pharmaceutically acceptable carrier.

11. A method of treating inflammations of the skin comprising applying to the affected area of skin a composition comprising an effective amount of at least one compound of claim 1 and a pharmaceutically acceptable carrier.

* * * * *